United States Patent [19]

Brown et al.

[11] 4,146,634

[45] Mar. 27, 1979

[54] COMPOSITION

[75] Inventors: Kenneth Brown; David J. Robinson; James E. Taylor, all of Loughborough, England

[73] Assignee: Fisons Limited, London, England

[21] Appl. No.: 810,361

[22] Filed: Jun. 27, 1977

Related U.S. Application Data

[63] Continuation-in-part of Ser. No. 626,786, Oct. 29, 1975, abandoned, and a continuation-in-part of Ser. No. 626,789, Oct. 29, 1975, abandoned.

[30] Foreign Application Priority Data

Nov. 9, 1971 [GB] United Kingdom ............... 48595/71

[51] Int. Cl.² ............................................ A61K 31/35
[52] U.S. Cl. .................................................. 424/283
[58] Field of Search ....................................... 424/283

[56] References Cited

U.S. PATENT DOCUMENTS

| | | | |
|---|---|---|---|
| 3,686,412 | 8/1972 | Fitzmaurice et al. | 424/283 |
| 3,705,945 | 12/1972 | Fitzmaurice et al. | 424/283 |
| 3,777,033 | 12/1973 | Fitzmaurice et al. | 424/283 |
| 3,792,063 | 2/1974 | Cairns et al. | 424/283 |
| 3,948,954 | 4/1976 | Cairns et al. | 424/283 |

OTHER PUBLICATIONS

Easty et al., Clinical Allergy, 1972, vol. 2, pp. 99–107.
Merck Manual, 12th Ed., 1972, pp. 972–976.
Stedman's Medical Dictionary, 1966, p. 1520.

*Primary Examiner*—Stanley J. Friedman
*Attorney, Agent, or Firm*—Merriam, Marshall & Bicknell

[57] ABSTRACT

A pharmaceutical composition in the form of a lozenge, chewable tablet, chewing gum, pastille, gel, paint or paste comprises from 0.01 to 20% by weight of 1,3-bis(-carboxychromon-5-yloxy)-2-hydroxypropane or a pharmaceutically acceptable salt thereof in association with a suitable pharmaceutically acceptable adjuvant, diluent or carrier. The composition is useful for the treatment of mouth ulcers in man.

1 Claim, No Drawings

COMPOSITION

This application is a continuation-in-part of our copending applications Ser. No. 626,786, filed Oct. 29, 1975, and Ser. No. 626,789, filed Oct. 29, 1975, both now abandoned.

This invention concerns pharmaceutical compositions.

1,3-Bis(2-carboxychromon-5-yloxy)-2-hydroxypropane and the pharmaceutically acceptable salts thereof are known compounds which are described and claimed in British Pat. No. 1,144,905. The compounds are known to be of use in the treatment of medical disorders caused or exacerbated by products which arise from the combination of certain types of antibody with specific antigen. In man, it has been found that the disodium salt of 1,3-bis-(2-carboxychromon-5-yloxy)-2-hydroxypropane is of exceptional merit when administered by inhalation in the treatment of asthma.

We have now found that 1,3-bis(2-carboxychromon-5-yloxy)-2-hydroxypropane and the pharmaceutically acceptable salts thereof are surprisingly of use in the treatment in man of aphthous stomatitis (mouth ulcers).

Accordingly, this invention provides a pharmaceutical composition in the form of a lozenge, chewable tablet, chewing gum, pastille, gel, paint or paste comprising from 0.01 to 20% by weight of 1,3-bis(2-carboxychromon-5-yloxy)-2-hydroxypropane or a pharmaceutically acceptable salt thereof in association with a suitable pharmaceutically acceptable adjuvant, diluent or carrier.

Pharmaceutically acceptable salts of the bis-chromone include the alkali-metal, for example sodium or potassium, salts and the alkaline earth metal, for example calcium or magnesium, salts. An especially preferred salt is the disodium salt.

Those compositions which are gels, paints or pastes will naturally be applied directly to the afflicted site, whereas those compositions which are lozenges, chewable tablets, chewing gums or pastilles will be dissolved or dispersed in the mouth to give a significant concentration of the active ingredient over the afflicted site. The compositions which are to be applied directly to the afflicted site are desirably so formulated that they are not easily washed from the site, and those which are to be dissolved or dispersed in the mouth are desirably so formulated as to give a significant concentration of the active ingredient in the mouth over as long a period as possible.

The lozenge, chewable tablet, chewing gum and pastille compositions of the present invention preferably contain from 0.2 to 5%, more preferably from 1 to 4%, for example from 1.5 to 2.5%, by weight of the bis-chromone. On the other hand, the gel, paint and paste compositions of the present invention preferably contain from 0.5 to 15%, more preferably from 1 to 5%, for example from 1.5 to 2.5%, by weight of the bis-chromone.

In general, it is believed that a skilled formulation chemist would be able to produce a satisfactory composition having the desired parameters. However, the following details are given for further guidance as to the preferred compositions.

The lozenges desirably have a disintegration time in the British Pharmacopoeia Disintegration Test of greater than 10 minutes, and more preferably of greater than 15 minutes. The lozenges also desirably have a hardness as measured by Monsanto Hardness Tester of greater than 5 kg, and more preferably of greater than 7 kg. The hardness is desirably not greater than 11 kg.

The carrier for the lozenges is conveniently a sugar, such as glucose, lactose or sucrose, or a substantially non-cariogenic material, for example mannitol, xylitol or polyethylene glycol.

In addition to the active ingredient and the carrier, the lozenges preferably contain one or more binders, such as gelatin or liquid glucose BPC 1963, which in total may conveniently be present in an amount of from 0.5 to 10% weight of the lozenge. A preferred range is from 1 to 5% by weight.

The lozenges may additionally contain a lubricant, such as stearic acid or a stearate such as magnesium stearate to facilitate manufacture of the lozenge. When one or more lubricants are present, the total content thereof in the lozenge is preferably from 0.1 to 5% by weight.

The lozenges may be prepared by conventional lozenge making procedures, for example by admixing the 1,3-bis(2-carboxychromon-5-yloxy)-2-hydroxypropane or salt thereof with the adjuvant, diluent or carrier and compressing the mixture. In a preferred procedure, the bis-chromone and the adjuvant, diluent or carrier are desirably first granulated together before being compressed into the lozenge. The granulation step is preferably a wet granulation step, and a lubricant is desirably added immediately before the compression step.

The chewable tablets preferably have a disintegration time in the British Pharmacopocia Disintegration Test of greater than 10 minutes and more preferably of greater than 15 minutes.

The carrier for the chewable tablets is desirably one or more of mannitol, polyethylene glycol or cellulose. The carrier is preferably present in an amount of greater than 50% by weight of the chewable tablet, and is more preferably present in an amount of from 60 to 85% by weight thereof.

In addition, a binding agent, for example gelatin or a cellulose derivative, such as methyl cellulose or methyl hydroxyethyl cellulose, is preferably present, desirably in an amount of from 0.5 to 20%, more especially from 0.5 to 4%, by weight of the chewable tablet.

The chewable tablets may be prepared by conventional tabletting procedures. For example, the dry ingredients may simply be admixed and compressed to an appropriate hardness.

The chewing gum formulations comprise the active ingredient dispersed homogeneously throughout a latex. Most preferably, the active ingredient is made first into a concentrated aqueous solution thereof, which is then dispersed in the latex by a conventional blending procedure. The latex employed is preferably chicle gum or jelutong gum or a mixture of both.

The lozenge and chewable tablet formulations preferably contain the bis-chromone in finely-divided form having a mass median diameter of less than 10 microns. The carrier in the lozenge and chewable tablet formulations is also preferably employed in finely-divided form, having a mass median diameter of less than 150 microns.

The pastilles contain from 8 to 30% by weight of a pharmaceutically acceptable gelling agent, and more preferably from 15 to 25% thereof. Desirably, the gelling agent is gelatin. The pastilles preferably also contain from 10 to 60% by weight, more preferably from 30 to 50% by weight of a softening agent, for example glycerol.

The carrier is preferably water.

The pastilles may be prepared by conventional procedures. For example, the gelling agent may be dissolved in the carrier at elevated temperature, the other components then added, and the solution poured into moulds and allowed to cool.

The lozenges, chewable tablets, chewing gums and pastilles of the present invention may also contain an adherant, which may be a cellulose derivative such as methyl cellulose, ethyl cellulose or hydroxypropylmethyl cellulose which enables the composition, when dissolved in the mouth, to adhere slightly to the afflicted surfaces of the mough, and thereby increase the contact time between the active ingredient and the afflicted site. The adherent may be present in an amount of from 0.1 to 5% by weight.

The dosage of active ingredient to be administered will of course depend upon the severity of the affliction. However, a dosage of from 0.1 mg to 200 mg, preferably 2 to 200 mg, of the bis-chromone administered in lozenges, chewable tablets, chewing gum or pastilles 1 to 4 times a day (i.e. a preferred daily dosage of from 0.1 mg to 800 mg) is generally found to be satisfactory.

The gel compositions of the present invention contain from 0.5 to 20%, preferably from 0.5 to 10%, for example from 1 to 5% by weight of a pharmaceutically acceptable gelling agent.

The gelling agent employed, which may be any pharmaceutically acceptable gelling agent, is preferably present in the composition in such an amount that the composition is neither so mobile that it runs off the site to which it is applied nor so stiff that it cannot easily be dispensed or applied. Although the amount to be incorporated for best results will vary with the particular gelling agent employed, it is believed to be within the competence of any skilled formulation chemist to produce a composition having the desired characteristics.

Typical gelling agents which may be employed include hydroxypropylmethyl cellulose, sodium carboxymethyl cellulose, carboxypolymethylene or PVM/MA (a copolymer of methyl vinyl ether and maleic anhydride).

The carrier employed is preferably water, although other carriers may be employed if desired, for example glycerol, propylene glycol or a paraffin base.

The gels of the present invention preferably contain a complexing agent, for example the disodium salt of ethylenediamine tetraacetic acid (EDTA), since this prevents the formation of insoluble heavy metal salts of the bis-chromone. The complexing agent is preferably present in an amount of from 0.01 to 0.1% by weight of the gel.

The gels may be prepared by conventional gel-forming procedures, for example by dissolving the 1,3-bis(2-carboxychromon-5-yloxy)-2-hydroxypropane or salt thereof at an elevated temperature in the carrier, and cooling the solution to form the desired gel.

The paints of the present invention contain a liquid carrier, for example water, and a thickening agent, for example glycerol, soldium carboxymethylcellulose or pothyethylene glycol in an amount of from 0.5 to 2.0% by weight of the paint.

The paints may be prepared by conventional paint-forming procedures. For example, the ingredients may be mixed and blended to the desired consistency.

The paste compositions of the present invention contain one or more thickening agent, for example gelatin, pectin, zinc oxide, polyethylene glycol, starch, bentonite or a cellulose derivative such as carboxymethyl cellulose, in an amount in total of from 2 to 30% by weight of the paste, and an aqueous or liquid paraffin base.

The paste composition may be prepared by conventional paste-forming procedures. Thus, for example, the ingredients may simply be admixed, with heating if necessary to give a homogeneous product followed by cooling, to give the desired paste. Any insoluble materials in the paste should desirably have a mass median diameter of less than 150 microns.

The dosage to be administered will depend to some extent on the severity of the affliction to be treated. However, a dosage of from 0.5 mg to 30.0 mg, preferably 1.5 mg to 20.0 mg of the bis-chromone, administered in a gel, paint or paste directly on the afflicted site 1 to 4 times a day (i.e. a preferred daily dosage of from 1.5 mg to 80.0 mg) is generally found to be satisfactory.

Naturally, the compositions of the present invention may also contain flavouring or colouring agents, preservatives, or other medicaments as desired.

All the components of the compositions of the present invention are desirably sterile.

This invention is further described, though only by way of illustration, in the following Examples.

EXAMPLE 1

The following ingredients were formulated into a 1 gm lozenge as described below:

|  | % w/w |
|---|---|
| 1,3-bis(2-carboxychromon-5-yloxy)-2-hyroxy-pyropane, disodium salt (mass median diameter <10 microns) | 2.0 |
| Sucrose (mass median diameter <150 microns) | 95.83 |
| Gelatin | 0.64 |
| Liquid glucose BPC 1963 | 0.64 |
| Stearic acid (powdered) | 0.64 |
| Peppermint oil | 0.25 |
|  | 100.00 |

The gelatin and liquid glucose were dissolved in water to give a 10% w/v solution with respect to each. The sucrose, disodium salt and stearic acid were independently mixed intimately and added to the solution. This mixture, after stirring to mix the components, was then passed through a coarse sieve to give coarse particles, which were dried. Finally the peppermint oil was added, further mixing was effected, and a lozenge was produced by compressing the mix in a die to a Monsanto hardness of 7 kg in a conventional manner.

The lozenge which resulted was of pleasant, acceptable taste, had good 'mouth feel', and dissolved in the mouth over a period of about 10 minutes.

EXAMPLE 2

The following ingredients were formulated into a chewable tablet as described below:

|  | mg |
|---|---|
| 1,3-bis(2-carboxychromon-5-yloxy)-2-hydroxypropane, disodium salt (mass median diameter <10 microns) | 20.0 |
| Milled mannitol | 480.0 |
| Methyl cellulose 20 cp | 7.5 |
| Polyethylene glycol 6000 (micronised) | 50.75 |
| Flavouring | 1.95 |
|  | 560.20 |

The ingredients were admixed and blended to homogeneity, and the mixture was then compressed to a Monsanto hardness of 5 kg in a conventional die. A chewable tablet resulted of good acceptability.

EXAMPLE 3

The following ingredients were formulated into a chewing gum as described below:

| | g |
|---|---|
| 1,3-bis(2-carboxychromon-5-yloxy)-2-hydroxypropane, disodium salt (mass median diameter <10 microns) | 0.4 |
| Chicle gum | 10.0 |
| Water | 2.0 |
| | 12.4 |

The disodium salt was dissolved in the water by heating, and the solution was added to the melted Chicle gum. The mixture was then blended to homogeneity and was cast into sticks. On cooling a chewing gum resulted of acceptable quality.

EXAMPLE 4

The following ingredients were formulated into pastilles as described below:

| | % w/w |
|---|---|
| 1,3-bis(2-carboxychromon-5-yloxy)-2-hydroxypropane, disodium salt | 4.0 |
| Gelatin | 16.0 |
| Glycerol | 40.0 |
| Water | 40.0 |
| Flavouring | q.s. |
| | 100.0 |

The gelatin, glycerol and water were heated together on a water bath to give a clear solution. The disodium salt was then dissolved in the solution, and the resultant solution was poured into a pastille mould. On cooling, pastilles were formed of good acceptability.

EXAMPLE 5

The following ingredients were formulated into a gel as described below:

| | % w/w |
|---|---|
| 1,3-bis(2-carboxychromon-5-yloxy)-2-hydroxypropane, disodium salt | 2.00 |
| Disodium salt of ethylenediamine tetraacetic acid | 0.01 |
| Hydroxypropylmethyl cellulose (5000 cp) | 2.00 |
| Water | 95.99 |
| | 100.00 |

The bis-chromone and the disodium salt of ethylenediamine tetraacetic acid were dissolved in part of the water, and the solution was heated to 95° C. The hydroxypropyl methyl cellulose was then dispersed into this solution, and the mixture was cooled with stirring in such a way as to avoid the incorporation of air. The remainder of the water was then added, and the mixture cooled to 4° C. overnight, with stirring to avoid the incorporation of air, to allow the hydroxypropyl methyl cellulose to dissolve. A gel resulted of appropriate physical characteristics to render it suitable for application in the mouth.

EXAMPLE 6

The following ingredients were formulated into a paint as described below:

| | % |
|---|---|
| 1,3-bis(2-carboxychromon-5-yloxy)-2-hydroxypropane, disodium salt | 2.0 |
| Ethyl alcohol (90%) | 20.0 |
| Glycerol | 20.0 |
| Purified water | 58.0 |
| | 100.0 |

The disodium salt was dissolved in part of the water, and the ethyl alcohol and glycerol were then added to the solution. Finally, the remainder of the water was added to give a paint of acceptable characteristics.

EXAMPLE 7

The following ingredients were formulated into a paste as described below:

| | % w/w |
|---|---|
| 1,3-bis-(2-carboxychromon-5-yloxy)-2-hydroxypropane, disodium salt (mass median diameter <10 microns) | 5.0 |
| Bentonite | 10.0 |
| Glycerol | 10.0 |
| Distilled water | 75.0 |
| | 100.0 |

The bentonite was heated at 150° C. for 1 hour to sterilise it, and was then mixed with the disodium salt. The glycerol was then added with trituration, followed by the water. A paste resulted of acceptable quality.

We claim:

1. A method of treating mouth ulcers in man, which method comprises applying to the afflicted site an effective amount of 1,3-bis(2-carboxychromon-5-yloxy)-2-hydroxypropane or a pharmaceutically acceptable salt thereof, by means of a pharmaceutical composition in the form of a lozenge, chewable tablet, chewing gum, pastille, gel, paint or paste comprising from 0.01 to 20% by weight of 1,3-bis(2-carboxychromon-5-yloxy)-2-hydroxypropane or a pharmaceutically acceptable salt thereof in association with a suitable pharmaceutically acceptable adjuvant, diluent or carrier.

* * * * *

UNITED STATES PATENT AND TRADEMARK OFFICE
CERTIFICATE OF CORRECTION

PATENT NO. : 4,146,634
DATED : March 27, 1979
INVENTOR(S) : Kenneth Brown et al.

It is certified that error appears in the above-identified patent and that said Letters Patent are hereby corrected as shown below:

Under "Foreign Application Priority Data", -

"Nov. 9, 1971 [GB] United Kingdom ....48595/71"

should be

-- Nov. 9, 1974 [GB] United Kingdom.....48591/74

Nov. 9, 1974 [GB] United Kingdom.....48595/74--

Signed and Sealed this

Twenty-fifth Day of December 1979

[SEAL]

Attest:

SIDNEY A. DIAMOND

Attesting Officer

Commissioner of Patents and Trademarks